US006849451B2

(12) United States Patent
Wagner et al.

(10) Patent No.: US 6,849,451 B2
(45) Date of Patent: Feb. 1, 2005

(54) HYBRID CELLS

(75) Inventors: Thomas E. Wagner, Greer, SC (US);
Yanzhang Wei, Greer, SC (US)

(73) Assignee: Greenville Hospital System,
Greenville, SC (US)

(*) Notice: Subject to any disclaimer, the term of this patent is extended or adjusted under 35 U.S.C. 154(b) by 0 days.

(21) Appl. No.: 09/756,293

(22) Filed: Jan. 9, 2001

(65) Prior Publication Data

US 2001/0049142 A1 Dec. 6, 2001

Related U.S. Application Data

(60) Provisional application No. 60/175,376, filed on Jan. 11, 2000.

(51) Int. Cl.$^7$ .............................. C12N 5/02; C12N 5/06; C12N 5/12; C12N 15/02; A01N 65/00; A01N 33/48; A01N 21/75; A01N 21/76
(52) U.S. Cl. ........................ 435/346; 435/325; 435/347; 435/440; 435/449; 424/93.1; 436/63; 436/164; 436/172
(58) Field of Search .......................... 436/63, 164, 172; 435/346, 347, 325, 440, 443; 424/93.1

(56) References Cited

U.S. PATENT DOCUMENTS

| 4,762,701 A | 8/1988 | Horan et al. ................. 424/1.1 |
| 4,783,401 A | 11/1988 | Horan et al. ................. 435/34 |
| 4,859,584 A | 8/1989 | Horan et al. ................. 435/29 |
| 6,197,593 B1 * | 3/2001 | Deka et al. |
| 6,652,848 B1 | 11/2003 | Gong et al. |

FOREIGN PATENT DOCUMENTS

| WO | WO 90/03576 | 4/1990 |
| WO | WO 96/30030 | 10/1996 |
| WO | WO 98/46785 | 10/1998 |

OTHER PUBLICATIONS

Koolwijk et al. enrichment and selection of hybrid hybridomas by percoll density gradient centrifugation and foluroescent–activated cell sorting pp. 217–225 No. 2 1988.*
Ohkohchi et al. New technique for producing hybridoma by using laser radiation Apr. 18. 2002.*
Wagner et al. A somatic cell hybrid panel for distal 17q: GDIA1 maps to 17q25.3 pp. 172–175 1997.*
Abbas et al, Cellular and Molecular Immunology, 1999.*
Schaap, G. H. t al., *Differentiation*, "Gene Expression in Flow Sorted Mouse Terato Carcinoma X Human Fibroblast Heterokaryons" 1984, vol. 26, No. 2, pp. 127–133.
Holmes L. M. et al., *Journal of Immunotherapy*, "A rapid, Novel Strategy to Induce Tumor Cell–Specific Cytotoxic T Lymphocyte Responses Using Instant Dendritomas." Mar.–Apr. 2001) vol. 24, No. 2, pp 122–129.
Stryer, *Biochemie*, Spektrum der Wissenschaften GmbH, 1990, pp. 931–933.

Parkinson et al., "Cytokines: Biology And Applications in Cancer Medicine", in Cancer Medicine, 4$^{th}$ ed., pp. 1213–1226.
Philip et al., "Treatment Of Malignant Melanoma With Interleukin–2," *Seminars in Oncology*, vol. 24(1):S4–32–Sr–38, (1997.
Smith et al., "Immune And Gene Therapy For Melanoma, And The Immunobiology Of Melanoma", *Internaitonal Journal Of Dermatology*, Blackwell Science Ltd., vol. 38:490–508, (1999).
Boon et al., "Tumor Antigens Recognized By T Cells", Elsevier Science Ltd., vol. 18:267–268, (1997).
Stockert et al., "A Survey Of The Humoral Immune Response Of Cancer Patients To A Panel Of Human Tumor Antigens", *J. Exp. Med.*, The Rockefeller University Press, vol. 187(8):1349–1354, (1998).
Sahin et al., "Human Neoplasms Elicit Multiple Specific Immune Responses In The Autologous Host", *Proc. Natl. Acad. Sci. USA*, Immunology, vol. 92:11810–11813, (1995).
Gabrilovich et al., "Production of Vascular Endothelial Growth Factor By Human Tumors Inhibits the Functional Maturation Of Dendritic Cells", *Nature Medicine*, vol. 2(10):1096–1103, (1996).
Ishida et al., "Defective Function Of Langerhans Cells in Tumor–Bearing animals Is The Result of Defective Maturation From Hemopoietic Progenitors", *The Journal of Immunology*, The American Association of Immunologists, pp. 4842–4851, (1998).
Steinman, "The Dendritic Cell System And Its role In Immunogenicity", *Annu. Rev. Immunol.*, Annual Reviews Inc., vol. 9:271–296, (1991).
Macatonia et al., "Primary Stimulation By Dendritic Cells Induces Antiviral proliferative And Cytotoxic T Cell Responses in Vitro", *J. Exp. Med.*, The Rockefeller University Press, vol. 169:1255–1264, (1989).
Mehta–Damani et al., "Generation Of Antigen–Specific CD8+ CTLs From Naïve Precursors", *The Journal of Immunology*, The American Association Of Immunologists, vol. 153:996–1004, (1994).
Porgador et al., "Bone Marrow–Generated Dendritic Cells Pulsed With A Class I–Restricted peptide Are Potent Inducers Of Cytotoxic T Lymphocytes", *J. Exp. Med.*, The Rockefeller University Press, vol. 182:255–260, (1995).
Young et al., "Dendritic Cells As Adjuvants For Class I Major Histocompatibility Complex–Restricted Antitumor Immunity", *J. Exp. Med.*, The Rockefeller University Press, vol. 183:7–12, (1996).

(List continued on next page.)

*Primary Examiner*—Q. Janice Li
(74) *Attorney, Agent, or Firm*—Foley & Lardner LLP (57) ABSTRACT

A rapid, simple-to-use method for preparing hybrid cells, applicable to fully differentiate, non-dividing cells, entails bringing at least two different cells into contact under conditions that promote cell fusion and then purifying the resultant hybrid without antibiotic or metabolic selection. This approach yields hybrid cells useful in a variety of applications, including clinical treatment regimens, as cellular modulators of the immune system.

14 Claims, 3 Drawing Sheets

OTHER PUBLICATIONS

Mayordomo et al., "Bone–Marrow–Derived Dendritic Cells Pulsed With Synthetic Tumour Peptides Elicit Protective And Therapeutic Antitumour Immunity", *Nature Medicine*, vol. 1(23):1297–1303, (1995).

Bakker et al., "Generation Of Antimelanoma Cytotoxic T Lymphocytes From health Donors After Presentation of melanoma–Associated Antigen–Derived Epitopes by Dendritic Cells in Vitro", *Cancer Research*, vol. 55:5330–5334, (1995).

Flamand et al., "Murine Dendritic Cells pulsed In Vitro With Tumor Antigen Induce Tumor Resistance in Vitro", *Eur. J. Immunol.*, VCH Veerlagsgeselischaft mbH, vol. 24:605–610, (1994).

Gong et al., "Induction Of Antigen–Specific Antitumor Immunity With Adenovirus–Transduced Dendritic Cells", *Gene Therapy*, Stockton Press, vol. 4:1023–1028, (1997).

Song et al., "Dendritic Cells Genetically Modified With An Adenovirus Vector Encoding The cDNA For A Model Antigen Induce Protective And Therapeutic Antitumor Immunity", *J. Exp. Med.*, The Rockefeller University Press, vol. 186(8):1247–1256, (1997).

Specht et al., "Dendritic Cells Retrovirally Transduced With A Model Antigen Gene Are Therapeutically Effective Against Established Pulmonary Metastases", *The Journal Of Experimental Medicine*, vol. 186(8):1213–1221, (1997).

Rosenberg et al., "Immunologic And Therapeutic Evaluation Of A Synthetic Peptide Vaccine For The Treatment of Patients With Metastatic Melanoma", *Nature Medicine*, vol. 4(3):321–327, (1998).

Wallack et al., "A Phase III Randomized, Double–Blind, Multiinstitutional Trial Of Vaccinia Melanoma Oncolysate-Active Specific Immunotherapy For Patients With Stage II Melanoma", *Cancer*, vol. 74(1):34–42, (1995).

Bystryn, "Clinical Activity of A Polyvalent Melanoma Antigen Vaccine", Springer–Verlag Berlin, vol. 139:337–348, (1995).

Mitchell, "Perspective On Allogeneic Melanoma Lysates in Active Specific Immunotherapy", *Seminars In Oncology*, vol. 25(6):623–635, (1998).

Morton et al., "Polyvalent Melanoma Vaccine Improves Survival Of Patients With Metastatic Melanoma", *Ann. N.Y. Acad. Sci.*, vol. 690:120–134 (1993).

Berd et al., "Autologous, Hapten–Modified Vaccine As A Treatment For Human Cancers", *Seminars in Oncology*, vol. 25(6):646–653, (1998).

Berd et al., "Autologous Hapten–Modified Melanoma Vaccine As Postsurgical Adjuvant Treatment After Resection Of Nodal Metastases", *Journal Of Clinical Oncology*, vol. 15(6):2359–2370, (1997).

Shurin, "Dendritic Cells Presenting Tumor Antigen", *Cancer Immunol. Immunother*, vol. 43:158–164, (1996).

Haigh et al., "Vaccine Therapy For patients With Melanoma", *Oncology*, vol. 13(11):1561–1574, (1999).

Gong et al., "Induction Of Antitumor Activity By Immunization With Fusions Of Dendritic And Carcinoma Cells", *Nature Medicine*, vol. 3(5):558–561, (1997).

Wang et al., "Eliciting T Cell Immunity Against Poorly Immunogenic Tumors By Immunization With Dendritic Cell–Tumor Fusion Vaccines", *The Journal Of Immunology*, The American Association of Immunologists, vol. 161:5516–5524, (1998).

Lespagnard et al., "Dendritic Cells Fused With Mastocytoma Cells Elicit Therapeutic Antitumor Immunity", *Int. J. Cancer*, vol. 76:250–258, (1998).

Rowse et al., "Tolerance And Immunity To MUC1 In A Human MUC1 Trangenic Murine Model", *Cancer Research*, vol. 53:315–321, (1998).

Abbas et al., "Cellular and Molecular Immunology", Saunders Text and Review Series, pp. 347–350.

Wei et al., "Long–Term Expression Of Human Growth Hormone (hGH) In Mice Containing Allogeneic Yolk Sac Cell Derived Neovascular Implants Expressing hGH", *Stem Cells*, vol. 14:2320238, (1996).

Horan et al., "Stable Cell Membrane Labelling", *Nature*, vol. 340:167–168, (1989).

Horan et al., "Fluorescent Cell Labelling For In Vivo And In Vitro Cell Tracking", *Methods In Cell Biology*, Academic Press, Inc., vol. 33:469–491, (1990).

Michelson et al., "In Vivo Tracking Of Platelets: Circulating Degranulated Platelets Rapidly Lose Surface P–Selectin But Continue To Circulate And Function", *Proc. Natl. Acad. Sci. USA*, vol. 93:11877–11882, (1996).

Zitvogel et al., "Therapy Of Murine Tumors With Tumor Peptide–Pulsed Dendritic Cells: Dependence On T Cells, B7 Costimulation, And T Helper Cell 1–Associated Cytokines", *J. Exp. Med.*, The Rockefeller University Press, vol. 183:87–97, (1996).

Gimmi et al., "Breast Cancer–Associated Antigen, DF3/MUC1, Induced Apoptosis Of Activated Human T Cells", *Nature Medicine*, vol. 2(12):1367–1370, (1996).

Yeh et al., "Expression of B7–1 Pam 212 Squamous Cell Carcinoma Enhances Tumor Cell Intractions With, Dendritic Epidermal T Cells But Does Not Affect In Vivo Tumor Growth", *J. Invest. Dermatol.*, vol. 109:728–733, (1997).

* cited by examiner

HYBRID CELLS

This is a non-provisional utility patent application claiming the priority of provisional patent application 60/175,376 filed Jan. 11, 2000, which is incorporated herein by reference.

BACKGROUND OF THE INVENTION

The present invention relates to hybrid cells and methods of making and using hybrid cells. Perhaps the most substantial practical application of hybrid cells is the production of hybridomas, which are used to produce monoclonal antibodies. In addition, they are used in a variety instances for research purposes, but their broader application, for example, in a clinical treatment setting has heretofore not been practical. These clinical applications include the cellular vaccines for treating or preventing cancer and other disorders, as well as preventing transplant rejection. The present invention responds to such deficiencies by providing methods and reagents that make the broad applicability of hybrid cells a reality.

Although a cancer treatment goal for more than half a century, recent advances in molecular immunology now make immunotherapy a truly viable option for the treatment of patients with cancer and metastatic disease. The past decade has seen the approval and introduction of several immunotherapeutic strategies for wide ranging use against several metastatic cancers, Parkinson et al., in CANCER MEDICINE, $4^{th}$ ed., pp. 1213–1226 (Holland et al., eds. 1997). Perhaps the best known strategies include IL-2 therapy (Philip et al., Seminars in Oncology. 24(1 Suppl 4): S32-8, 1997 February) and tumor vaccines targeted against melanoma. Smith et al., Int J Dermatol 1999; 38(7): 490–508. While these strategies are efficacious against some tumors, their potency is limited because they only enhance the already enfeebled ability of tumor cells to present their "foreign" epitopes to CD8 T-cells, and to generate thereby a tumor-specific cytotoxic T lymphocyte (CTL) response.

Autologous whole tumor cell-based vaccines were first used for immunotherapy of malignant melanoma. Such whole tumor cell-based vaccines are advantageous, because they contain large numbers of antigens, which eliminates the need for targeting the immune response against one antigen at a time. This is important because currently there is little ability to identify specific tumor-associated antigens (TAA) that are useful to induce immune system-mediated tumor regression. Boon et a., Immunol Today 1997; 18:267–268. To date, however, autologous whole tumor cell-based vaccines alone have shown only some isolated or marginal successes. Smith et al., supra. As seen below, the marginal success of whole tumor cell-based vaccines likely results from tumor cell mutations that impair their ability to act as antigen presenting cells ("APCs").

Evidence from many tumor immunology laboratories demonstrates that tumor cells persist in part because they have selected a mutation which partially or completely destroys their ability to act as APCs in the process of cytotoxic T lymphocyte CTL generation. Stockert et al., J. Exp. Med. 1998; 187: 1349–1354; Sahin et al., Proc. Natl Acad. Sci. USA 1995; 92:11810–11813; Gabrilovich et al., Nature Med. 1996; 2:1096–1103; Ishida et al., J. Immunol. 1998; 161:4842–4851. These observations spurred development of strategies that attempt to replace the tumor cell as the APC, rather than trying to boost the tumor's enfeebled antigen presenting process. The best candidate for such a replacement is the dendritic cell ("DC").

DCs are "professional" antigen presenting cells that play a vital role in stimulating immune responses. DCs not only can activate naive CD4+ T helper cells but also stimulate unprimed CD8+ cytotoxic T lymphocytes. Steinman, R. M. Annu. Rev. Immunol. 1991; 9, 271–296; Macatonia, et al., J. Exp. Med. 1988; 169, 1255–1264; Mehta-Damaniet al., J. Immunol. 1994;153, 996–1003; Porgador et al., J. Exp. Med. 1995;182, 255–260.

Because of these characteristics, DCs have been widely studied as antigen presenting cells for cancer immunotherapy. DCs can be loaded with tumor antigens by pulsing with whole tumor antigens or tumor antigen peptides. Young et al., J. Exp. Med. 1996; 183, 7–11; Mayordoma et al., Nat. Med. 1995;1, 1297–1302; Bakkar et al., Cancer Res. 1995; 55, 5330–5334; Flamand et al., Eur. J. Immunol. 1994; 24, 605–610; Gong et al, Gene Ther. 1997; 4, 1023–1028; Song et al., J. Exp. Med. 1997;186, 1247–1256; Specht et al J. Exp. Med. 1997;186, 1213–1256.

Peptide- or tumor lysate-pulsed dendritic cells have been used, for example, to vaccinate melanoma patients. Rosenberg et al., Nature Med 1998; 4: 321–327; Wallack et al., Cancer 1995; 75:34–42; Bystryn, Rec. Results Cancer Res. 1995; 139:337–348; Mitchell et al., Semin. Oncol. 1998; 25: 623–635; Morton et al., Ann. N.Y. Acad. Sci. 1993; 690:120–134; Berd et al., Semin Oncol. 1998; 25:646–653; Berd et al., J. Clin. Oncol. 1997; 15:2359–2370.

Tumor antigen-loaded DCs so loaded with tumor antigens are able to induce both cellular and humoral, antigen-specific, anti-tumor immune responses. Shurin, M. R. Cancer Immunol. Immunother. 1996; 43, 158–164. This approach, however, is limited to application against tumors expressing known tumor antigens. See, Haigh et al., Oncology 1999; 13, 1561–1573. It is worthless for those tumors with no identified tumor antigen, like primary tumors from patients, which constitute most real-world situations. Obviously alternative strategies are needed.

An additional problem with antigen pulsing techniques is that the antigen presenting system of an APC works more effectively and efficiently when the protein/antigen is synthesized inside the cell rather than outside the cell, a substantial drawback to using antigen-pulsed cells. In an effort to avoid this problem, a number of laboratories have attempted to use gene therapy to introduce specific tumor antigens into dendritic cells. Gong et al., 1997,Gene Ther. 4, 1023–28; Song et al, 1997, J. Exp. Med. 186: 1247–56; and Specht et al., 1997, supra. However, this gene therapy approach is also fraught with many disadvantages including: 1) the limited ability to identify all of the important specific tumor antigens, 2) the limited ability to map the genes of the specific tumor antigens, 3) only one or a small number of the known tumor antigen genes can be introduced into the dendritic cell and 4) the process is time-consuming and cumbersome.

On the other hand, fusions between DCs and tumor cells represents an alternative way to produce effective tumor antigen presenting cells by presenting the immune cells with all possible tumor antigens. Gong et al., Nat. Med. 1997; 3: 558–561; Wang et al., J. Immunol. 1998;161, 5516–5524; Lespagnard et al., Int. J. Cancer 1998; 76, 250–258; Rowse et al., Cancer Res. 1998; 58, 315–321. DCs have been fused with tumor cells and the fused cells efficiently presented tumor antigens to the immune cells and stimulated a specific anti-tumor immune responses. Gong et al.; Wang et al.; Lespagnard et al., all supra.

These fusion schemes, however, rely on selectable markers (gene products which render the cell resistant to specific cell toxins or allow them to grow under certain metabolic conditions) in each of the DCs and the tumor cells to isolate the resultant hybrid. The rare cell fusion products are selected by long-term culture in the presence of both cell toxins where only the fusion product, containing both selectable markers, can survive. Since the introduction and selection schemes using markers requires culture and multiple cell division, they cannot be applied to dendritic cells, because DCs are terminally differentiated, non-dividing cells. Thus, it is no surprise that the previous fusion work relied on well-defined tumor cell lines, bearing such a marker, and DC- and tumor-specific conjugated antibodies, which limits the usefulness of this strategy in cancer treatment.

In summary, the previous cancer-based fusion protocols have the following limitations: 1) they require established tumor cell lines which show specific marker(s); 2) they require both DC and tumor cell specific antibodies to select the fused cells; 3) the selection and expansion of the fused cells takes an impractical amount of time.

The area of preventing transplant rejection using hybrids are even less well-developed than cancer. In fact, no report of such has been found.

Typical approaches to preventing transplant rejection utilize non-selective immunosuppressive drugs that suppress the entire immune system. Abbas et al., CELLULAR AND MOLECULAR IMMUNOLOGY, pp. 347–350. Such approaches have the obvious disadvantage of making the patient more susceptible to disorders that otherwise could have been warded off by an intact immune system.

It has been recognized that at least two interactions must take place in order for an antigen presenting cell to activate a T cell. These interactions are between an antigen-loaded major histocompatibility (MHC) antigen and the T cell receptor, and between certain accessory molecules and their cognate receptors on the T cell. The best studied class of these accessory molecules is B7 (B7.1 and B7.2), which interact with CD28 and CTLA4 on T cells. Abbas et al., supra. Thus, disruption of either the MHC or the accessory interaction should result in a non-response useful, for example, in preventing transplant rejection.

In fact, disruption of B7 interaction not only prevents an immune response, it induces permanent tolerance to any antigen presented during the disruption. Wei et al., 1996, Stem Cells 14: 232–38. Thus, in the context of transplant rejection, blocking B7 should result in tolerance, preventing rejection. The problem with such an approach, and the likely reason that it has not be attempted clinically, is that tolerance would pertain to any antigen presented during treatment, not just to transplant antigens. In other words, if a patient were exposed to a pathogen during the B7 disruption, the patient's immune system would be rendered tolerant to the pathogen, permanently. This would prevent the patient from warding off the pathogen, having perhaps lethal consequences. Clearly, a more specific approach is needed.

A promising approach takes advantage of antigen presentation by cells that lack accessory molecules, like B7. These cells present antigen in the context of MHC, yet, because they lack the accessory interactions required for activation, they induce tolerance specific to the antigen presented. Thus, it is possible to load these cells, which include immature (naïve) B cells, with a specific antigen, and induce antigen-specific anergy. As with the cancer example described above, this antigen-by-antigen approach does not have the general applicability needed for practical clinical use. A methodology is needed which is applicable to any transplant organ, irrespective of the immunogenic antigens the organ displays.

In view of the foregoing, it is evident that the art is in need of generally applicable, rapid methods for inducing and suppressing specific immune responses to whole cells and specific reagents for accomplishing these methods.

SUMMARY OF THE INVENTION

It is, therefore, an object of the invention to provide solutions to the aforementioned deficiencies in the art.

Further to this object, the invention provides a kit useful in preparing hybrid cells. In one aspect, the kit contains at least two essentially endotoxin-free dyes and instructions for preparing hybrid cells from reactant cells by a method that entails contacting reactant cells with one of said dyes, respectively. In another aspect, the kit contains at least two essentially endotoxin-free dyes and an agent that promotes cell fusion. The endotoxin-free dyes are preferably fluorescent dyes, such as cyanine dyes.

Also according to this object of the invention, a hybrid cell preparation is disclosed. In one embodiment, the preparation contains a hybrid cell having no more than n-1 selectable markers, where n represents the number of reactant cells used to form the hybrid and the preparation is substantially free of non-hybrid cells. In another embodiment, the preparation contains a hybrid of a primary tumor cell and an antigen presenting cell. In still another embodiment, the preparation contains a hybrid of a normal cell and an antigen-presenting cell which lacks an accessory factor required to generate a positive immune response. The normal cell may be isolated from a transplant organ. An additional embodiment is a preparation containing a hybrid between a pathogenic cell and an antigen-presenting cell, like a cell from parasite. One hybrid cell preparation is composed of a hybrid cell labeled with at least two different dyes, that are preferably fluorescent, like cyanine dyes. The hybrid cell my be derived from, for example, a dendritic cell or an immature B cell.

Still another aspect of the invention provided in accord with this object is a method of preparing a hybrid cell. One embodiment of the inventive method entails bringing at least two different cells into contact under conditions that promote cell fusion, and then purifying the resultant hybrid without the need for antibiotic or metabolic selection. In one aspect the method is accomplished using fluorescent dyes, like cyanine dyes, and the hybrids are isolated by fluorescence activated cell sorting. The methods can involve fusing reactant cell, like a macrophage, a dendritic cell, and an antigen presenting cell that lacks an accessory factor required to generate a positive immune response, with a second reactant cell, like a tumor cell, a pathogenic cell and a normal cell. The method is preferably accomplished in less than about 48 hours.

In still another aspect, the invention provides a method of treating cancer, that involves providing an inventive hybrid cell preparation that is derived reactant cell that is a cancer cell; and administering the hybrid cell to a cancer patient. The method may include adjunct treatment with a cytokine or lymphokine, like interleukin-2.

In yet another aspect, the invention contemplates a method of treating a disorder associated with the presence of a pathogenic organism that involves providing an inventive hybrid cell preparation that is derived from a cell isolated from said pathogenic organism and administering the cell to a patient. Again, the method may include adjunct treatment with a cytokine or lymphokine, like interleukin-2.

Also in accord with the object of the invention, the invention provides a method of inducing immune tolerance to an antigen that entails providing an inventive hybrid cell preparation that is derived from a cell that expresses an antigen against which immune tolerance is sought and administering said preparation to a patient. The cell against which immune tolerance is sought may be a cell from a transplant organ, where the patient needs an organ transplant.

DETAILED DESCRIPTION OF THE INVENTION

In one aspect, the present invention provides a rapid and efficient method of preparing hybrid cells that are useful in a variety of clinical and non-clinical applications. The hybrid cells are particularly useful in treatment regimes that invoke the immune system to treat or prevent disease. For instance, in a preferred embodiment, the inventive hybrid cells are used to treat cancer by fusing a cancer cell to an antigen presenting cell. In another embodiment, the inventive hybrid cells comprise a plasma cell and a cancer cell which, like conventional hybridomas, are useful in preparing monoclonal antibodies. In still another embodiment, the present hybrid cells comprise an antigen presenting cell that lacks an accessory component needed for an immunogenic response and a cell from an organ destined for transplant in a patient. These cells may be used to induce tolerance to the transplant cells, thereby reducing the incidence of transplant rejection. Kits for generating hybrid cells and for practicing the inventive methods also are provided.

Method of Preparing Hybrid Cells

The present invention contemplates a method of preparing hybrid cells that is rapid, simple to use, and applicable to fully differentiate, non-dividing cells. The inventive approach involves bringing at least two different cells ("reactant cells") into contact under conditions that promote cell fusion, and then purifying the resultant hybrid ("product cell") without antibiotic or metabolic selection. In general, the purification is accomplished in a relatively short period of time, for example, in less than about 24 to 48 hours, after exposure to conditions that promote fusion.

In a preferred embodiment, the method is accomplished with the aid of at least two different dyes, which can be fluorescent dyes. Thus, the method may entail separately contacting, each with a different dye, the two cell types to be fused. This pre-fusion labeling marks each cell with a different dye, and permits discrimination among each fusion parent cell and the hybrid fusion product: the reactant cells each are stained with one dye, and the product cells are stained with both. This way, the hybrid fusion product may be separated from the reactant cells, for example, by fluorescence activated cell sorting (FACS), and the like.

Dyes useful according to the invention have the characteristic of associating with a cell for a time sufficient to detect them in such association. In addition, useful dyes do not substantially diminish cell viability, with greater than about 50% cell viability being preferred. Typically, they are fluorescent dyes. One useful class of dyes comprises the so-called "cyanine" dyes. Cyanine dyes come in a variety of types that fluoresce at different wavelengths such that they can be individually or jointly detected when associated with a cell. Some exemplary cyanine dyes are found in Horan et al., U.S. Pat. No. 4,783,401 (1998), U.S. Pat. No. 4,762,701 (1988) and U.S. Pat No. 4,859,584 (1989), the structures of which are hereby specifically incorporated by reference.

Two particularly useful cyanine dyes are PKH26-GL and PHK2-GL, which may be obtained from the Sigma Chemical Co. These dyes are preferred because they have been widely studied and used. For instance, they have been used in animal studies in vivo for cell trafficking studies. Horan et al., *Nature* 1989; 340, 167–168; Horan et al., *Methods Cell Biol.* 1990; 33, 469–490; Michelson et al., *Proc. Natl. Acad. Sci. USA* 1996; 93, 11877–11882. In laboratory animals these dyes have been shown not to affect cell growth or function and not to migrate from the cells stained with these dyes to other cells (Horan et al., 1989), thus have low toxicity, a desirable quality for in vivo applications.

Dyes employed in vivo in accordance with the present invention should be free of endotoxin, as measured, for example, by the Limulus amaebocyte (LAL) assay. Typically, when the measured endotoxin level is less than about 1 ng/$\mu$g dye, and preferably less than about 0.1 ng/$\mu$g dye, then the dye is considered "endotoxin-free."

More generally, the dyes are essentially pyrogen-free, whether pyrogenicity is contributed by endotoxin or other pyrogens. Thus, a dye is considered "essentially pyrogen free" when the final formulation of hybrid cells labeled with the dye (in a form to be injected into a subject, for example) yields less than about 1 endotoxin unit (EU)/dose, but preferably less than about 0.1 EU/dose and most preferably less than about 0.05 EU/dose. Toxicity thresholds are informed by the fact that most in vivo methods contemplated herein result in less than about $10^{-8}$ g of these dyes, in association with cells, being introduced into a patient when undertaking the inventive methods of treatment.

Conventional cyanine dye labeling methodologies require the presence of cellular stabilizers (osmolarity regulating agents), like sugars (e.g., glucose or mannitol), amino acids and/or certain Goods buffers. See, for example, Horan et al., U.S. Pat. No. 4,783,401 (1998). The inventors discovered that dimethyl sulfoxide (DMSO) can substitute for such stabilizers. In particular, DMSO diluted in a standard culture medium may be used as a solvent for cyanine dyes, and it promotes efficient and stable uptake of dye without substantial loss of cell viability. A generally useful range of DMSO concentration is from about 10 to about 50%, but a preferred range is from about 20 to about 40%. The invention therefore also contemplates methods of labeling cells, and corresponding kits, with cyanine dyes using DMSO in place of the conventional stabilizers.

Once the reactant cells are labeled, they are put into contact with one another, under conditions that promote fusion. Such fusion-promoting conditions are well known to the artisan, and typically involve the addition of an agent that promotes cell fusion. These agents are thought to work by a molecular crowding mechanism to concentrate cells to an extent that they are in close enough proximity to cause fusion of cell membranes. While the invention contemplates any agent that meets these characteristics, exemplary useful agents are polymeric compounds, like polyethylene glycols. An effective amount of such an agent generally will be from about 20% to about 80% (w/v). A preferred range is from about 40% to about 60%, with about 50% being more preferred.

After hybrid cell formation, it is usually beneficial to isolate them from the un-fused reactant cells. In the case of cellular vaccines, for example, this purification substantially increases the potency. Purification may be accomplished by conventional FACS methodologies, for example.

The method explicitly contemplates hybrid cells of higher order, which are fusions between more than two cells. In each case, all that is needed is an additional dye that can serve as a marker for selection of the higher-order hybrid. For example, three different reactant cells labeled with three different dyes are used to form a "tribred," and so on. Thus, as used herein, the term "hybrid cell" contemplates fusions between two or more reactant cells.

Kits of the Invention

The present invention also relates to kits for labeling cells and for preparing hybrid cells. These kits are useful in implementing the inventive method of preparing hybrid cells. A labeling kit, for example, contains at least one dye, and may contain DMSO and instructions for labeling. The inventive hybrid cell preparation kit, comprises at least two essentially endotoxin-free and/or pyrogen-free dyes and instructions for preparing hybrid cells and/or it comprises an agent that promotes cell fusion.

Hybrid Cell Preparations

The invention further contemplates a hybrid cell preparation. In general, the preparation will be substantially free of reactant cells (less than about 50% reactant cells, but preferably less than about 10% to 25% reactant cells, and most preferably less than about 5% reactant cells). The inventive hybrid cells are prepared from reactant cells that may have a selectable marker, but need not. In any event, at least one reactant cell lacks such a marker. Thus, where n represents the number of reactant cells, in most cases, n-1 will represent the maximum number of selectable markers found in the hybrid cell. For example, where two reactant cells fuse to form a hybrid, the hybrid will contain no more than one selectable marker.

The phrase "selectable marker" is used here in its conventional sense, to refer to an antibiotic resistance or a metabolic marker, such as hypoxanthine phosphoribosyl transferase (HPRT), and the like. Selectable markers are endogenously produced, and do not include exogenously added materials, like dyes.

In one embodiment, the inventive hybrid cell preparation, comprises a primary tumor cell and an antigen presenting cell (APC) as reactants. Such hybrids may be used as cellular vaccines to induce an immune response against a tumor. The tumor cell may be of any type, including the major cancers, like breast, prostate, ovarian, skin, lung, and the like. The APC preferably is a professional APC, like a macrophage or a dendritic cell. Due to their superior antigen presentation capabilities, dendritic cells are more preferred. Both syngeneic and allogeneic fusions are contemplated as the inventors have discovered using a mouse model that both work equally well.

An additional embodied hybrid comprises a pathogenic cell and an APC. These hybrids also are useful as cellular vaccines. Again, antigen presenting cells, and dendritic cells, in particular, are favored. The pathogenic cell, on the other hand, may be of virtually any type. For example, it may be a bacterial cell (*Helicobacter*, etc.) that has had its cell wall removed. The pathogenic cell may be a fungal cell, like *Candida, Cryptococcus, Aspergillus* and *Alternaria*.

The pathogenic cell also may be a parasitic cell from, for example, trypanosomal parasites, amoebic parasites, miscellaneous protozoans, nematodes, trematodes and cestodes. Exemplary genera include: *Plasmodium; Leishmania; Trypanosoma; Entamoeba; Naeglaria; Acanthamoeba; Dientamoeba; Toxoplasma; Pneumocystis; Babesia, Isospora; Cryptosporidium; Cyclospora; Giardia; Balantidium; Blastocystis; Microsporidia; Sarcocystis; Wuchereria; Brugia; Onchocerca; Loa; Tetrapetalonema; Mansonella; Dirofilaria; Ascaris* (roundworm); *Necator* (hookworm); *Ancylostoma* (hookworm); *Strongyloides* (threadworm); *Enterobius* (pinworm); *Trichuris* (whipworm); *Trichostrongylus; Capillaria; Trichinella; Anasakis; Pseudoterranova; Dracunculus; Schistosoma; Clonorchis; Paragonimus; Opisthorchis; Fasciola; Metagonimus; Heterophyes; Fasciolopis; Taenia; Hymenolepis; Diphyllobothrium; Spirometra*; and *Echinococcus*.

In another embodiment, the inventive hybrid cell preparation comprises a target cell against which immune tolerance is desired and an antigen presenting cell that lacks an accessory factor needed for an immunogenic response. Typically these APCs lack B7 (e.g., B7. 1 or B7.2); exemplary cells are naive, immature B cells and fibroblasts, but any cell capable of presenting antigen (having MHC molecules), yet lacking an accessory molecule, will suffice. In the case of B7, specific antibodies are known, and the artisan will be well apprised of methods to ascertain whether any particular cell type lacks B7. Naïve B cells are preferred because they express high levels of MHC molecules and all the adhesive molecules known in the art to be necessary for efficient cell-cell contact.

In any event, the resultant hybrids have the ability to present antigen to the immune system, since they bear class I and class II MHC molecules, yet they will not have the ability to activate the immune system, since they do not have the necessary accessory markers, like B7 (CD28 or FLTA4 ligands). Thus, instead of inducing an immune response, these hybrids will induce apoptotic clearance, thereby rendering the immune system tolerant to the target cell antigens presented by these hybrids. Such immune cell hybrids are useful in treating autoimmune disorders like transplant rejection.

The inventive hybrid cell preparation may be made using a combination of dyes, as detailed above. Thus, the inventive hybrid cell may be labeled with at least two different dyes. These dyes are preferably fluorescent and, again, cyanine dyes are favored. Alternatively, hybrid cells may be prepared, for example, using cell surface markers differentially expressed on the reactant cells and corresponding antibodies to them. The antibodies may be used to pan sequentially for each marker. See, Gong et al., 1997, Nat. Med. 3: 558–61.

Methods of Treatment

The inventive methods and products are useful in methods of treatment and prophylaxis, and "treatment" is used herein to include "prophylaxis." Such a method basically involves administering to a patient a hybrid between a "target" cell and a second, typically antigen-presenting, cell. The "target" cell is one against which an immune response is sought. The immune response may be positive or negative, depending on the disorder to be treated. For example, a positive immune response is desirable in treating cancer or parasitic diseases, but a negative immune response is desirable in preventing transplant rejection.

One embodied method of treatment or prophylaxis pertains to cancer. This method entails administering to a patient an inventive hybrid cell, or hybrid cells prepared by the inventive method or kit. In one aspect, the administered hybrid cell has n-1 selectable markers, as described above. The hybrid cell may be labeled with at least two dyes.

An exemplary cancer treatment method involves labeling isolated neoplastic and immune cells with different dyes and forming a hybrid cell between the labeled cells. The hybrid cell is isolated and administered to a patient in an acceptable excipient. In order to avoid administration of viable cancer cells, it is advisable to lethally irradiate the tumor reactant cells prior to fusion. This step kills the cell, but does not prevent efficient presentation of the tumor antigen(s) by the resultant hybrid cell. Both syngeneic and allogeneic fusions are contemplated as the inventors have discovered using a mouse model that both work equally well.

The cancer treatment may be augmented, moreover, by using additional antineoplastic agents in conjunction with the hybrid cells. One class of such agents is immunomodulators. These include cytokines and lymphokines, especially interleukin-2 (IL-2) and IL-2 derivatives, like aldesleukin (Proleukin, Chiron Corp.). The use of IL-2 is preferred because it should further enhance the immune response generated by the hybrid cell. As used herein, "interleukin-2" is used generically to refer to the native molecules and any derivatives or analogs that retain essential interleukin-2 activity, like promoting T cell growth. Other lymphokines and cytokines may also be used as an adjunct to treatment. Examples include interferon gamma (IFN-$\gamma$), granulocyte macrophage colony simulating factor (GM-CSF), and the like.

A modification of the cancer treatment regimen can be used to treat any disorder associated with a pathogenic organism. In this modification, the reactant cells will be APCs and cells isolated from the pathogenic organism. Otherwise, the treatment would be accomplished as in cancer treatment.

A different aspect of the invention comprehends a method of treating autoimmune disorders. The method is accomplished in essentially the same manner as the cancer treatment set out above. The primary difference being the identity of the reactant cells. In the case of autoimmune disorders, the goal is to diminish or eliminate an immune response, whereas in cancer treatment the goal is to create or enhance an immune response.

The ability to use the inventive hybrids in treating autoimmune disorders derives in part from the observation that certain cells can present antigen, yet they lack the accessory molecules to provide a positive immune response. Typically these cells lack B7, and they may be immature B cells or fibroblasts, for example. In fact, antigen presentation by such cells generates a negative immune response. It tolerizes the immune system, inducing apoptosis of specific antigen-reactive immune cells.

Thus, the method of treating autoimmune disorders utilizes an APC, deficient in an accessory interaction, and a "normal cell" as the reactants. The "normal cell" is any target cell to which immune tolerance is desired. It may be from a transplant organ, for example, in a method of preventing transplant rejection. In the case of treating or preventing diabetes, by transplantation or otherwise, on the other hand, the normal cell may be an Islet cell. Such a method can be adapted to tolerize the immune system against any type of cell.

As used herein, the term "treat" and its various forms also encompasses prophylactic methods.

The foregoing detailed description and the following examples are offered for illustrative purposes and are not meant to be limiting. The artisan will recognize that there are additional embodiments that fall within the invention, but are not described with particularity.

EXAMPLES

Example 1

Animal Studies

This example demonstrates the preparation of certain hybrids between cancer cells and dedritic cells, called dendritomas. These hybrids are used as a cellular vaccine to prevent cancer in a murine metastatic cancer model system.

To prepare dendritic cells from bone marrow, the appropriate number of female C57BL/6J. mice to support later Dendritoma injections (two mice for every one mouse to be injected) were sacrificed. The femur and tibia of both hind legs were removed from each mouse. Bone marrow was flushed out of the bones using a syringe containing RPMI 1640 with 25 mM Hepes (Gibco BRL). The media containing the bone marrow was filtered through a 40 $\mu$m cell strainer into a 50 ml conical centrifuge tube. The bone marrow cells were pelleted by centrifugation at 1500 rpm for five minutes. After removing the supernatant, the tube was gently tapped to loosen the cell pellet. Red blood cell lysis was achieved by adding 5 ml/mouse of ACK Lysing Solution (0.15 M $NH_4Cl$, 1 mM $KHCO_3$, 0.1 mM $Na_2EDTA$, pH 7.3) and incubating at room temperature for five minutes. The cells were pelleted by centrifugation at 1500 rpm for five minutes. The supernatant was removed, and the cells were gently resuspended in 10 ml/mouse of complete DC media (RPMI 1640, 10% fetal bovine serum (FBS), 100 $\mu$g/ml gentamicin, 10 ng/ml GM-CSF, 10 ng/ml IL-4). The cells were plated into two wells/mouse of a six well tissue culture plate. After incubating the cultures overnight at 37° C., 5% $CO_2$, the floating cells were removed from each culture. Adherent cells were washed twice with 1× Phosphate Buffered Saline (PBS). Each well of cells was fed 5 ml of complete DC media. The cultures were incubated for 48 hours at 37° C., 5% $CO_2$. The dendritic cells were harvested from the 6 well plate by removing the supernatant containing the cells to a 15 ml conical centrifuge tube. Each well was washed twice with 3 ml of 1× PBS. The cells were lightly trypsinized by adding 1 ml of 0.25% Trypsin/EDTA (Gibco BRL) to each well. After rocking the plate to cover the entire surface, the trypsin solution was quickly removed from the plate. The plate was lightly tapped to remove any loosely attaching cells. These cells were resuspended in 2 ml of complete DC media and added to the 15 ml tube. The cells were pelleted by centrifugation at 1500 rpm for five minutes. After resuspending the cells in 10 ml of complete DC media, a cell count was taken.

B16F0 murine melanoma cells were obtained from the ATCC (CRL-6322) and cultured using standard tissue culture techniques. When the cells were ready for use, they were trypsinized using 0.25% Trypsin/EDTA. After taking a cell count the number of cells needed for experimentation were pelleted by centrifugation at 1500 rpm for five minutes. The remaining cells were cultured for later use.

For general cell membrane labeling of murine dendritic cells and B16F0 melanoma cells, a commercial fluorescent cell linker kit was used. The dendritic cells were labeled fluorescent green using Sigma stock number PKH2-GL; the B16F0 melanoma cells were labeled fluorescent red using Sigma stock number PKH26-GL. The staining procedure was performed at 25° C. The cells to be stained were washed with serum-free media. The cell suspension was centrifuged at 400 g for five minutes to obtain a loose pellet. Supernatant was removed leaving less than 25 $\mu$l of medium on the pellet. The pellet was resuspended by tapping the tube, and 1 ml of Diluent A or C for green or red staining respectively was added to resuspend the cells. Immediately prior to staining, $4\times10^{-6}$ molar dyes (2×) were prepared with Diluent A or C in polypropylene tubes. To minimize ethanol effects, the amount of dye added was less than 1% of the individual sample volume. The cells in the diluent were rapidly added into 1 ml of 2× dye. The cells and dye were immediately mixed by gentle pipetting. The mixture was then incubated at 25° C. for five minutes. The staining process was stopped by adding an equal volume of FBS and incubating for one minute. The stained cells were diluted with equal volume of complete culture medium. Stained cells were removed from the staining solution by centrifuging at 400 g for 10 minutes. After a total of three washes, the cells were resuspended in complete medium at a proper concentration. Efficiency of staining was monitored by fluorescent microscopy.

Prior to the fusion process, the red fluorescently stained B16F0 murine melanoma cells were irradiated with 5,000 rads. Murine dendritic cells and B16F0 melanoma cells were fused together by mixing the two cell types at a 1:1 ratio in a 50 ml conical centrifuge tube. The tube was filled with serum-free RPMI 1640 with 25 mM Hepes. The cell mixture was centrifuged at 1500 rpm for five minutes at room temperature. Note that during the fusion process, all solutions as well as the tube in which the fusion was performed were kept at 37° C. using double-beaker water baths. The supernatant from the mixed cell pellet was aspirated and discarded. Using a 1 ml serological pipet, 1 ml of prewarmed 50% PEG/DMSO (Sigma), which contains 50% PEG and 10% DMSO in PBS ($Ca^{++}$- and $Mg^{++}$-free), was added to the mixed cell pellet drop-by-drop over one minute, stirring the cells with the pipet tip after each drop. The mixture was stirred for an additional minute with the pipet.

Using a clean 2 ml serological pipet, 2 ml of prewarmed serum free RPMI 1640 with 25 mM Hepes was added to the cell mixture drop-by-drop over two minutes, stirring after each drop. With a 10 ml serological pipet, 7 ml of prewarmed serum free RPMI 1640 with 25 mM Hepes was added drop-by-drop over two to three minutes. The cells were pelleted by centrifugation at 1500 rpm for five minutes at room temperature. The supernatant was discarded, and the tube was placed back into the beaker water bath. With a clean 10 ml serological pipet, the cell pellet was resuspended in 10 ml of complete DC media by forcefully discharging about 3 ml of media onto the pellet and then gently adding the remaining media. The resuspended cells were put into a T75 tissue culture flask. The Instant Dendritomas (fused dendritic cells with melanoma cells) were incubated overnight at 37° C., 5% $CO_2$. A drop of the cells was placed on a slide and evaluated by fluorescent microscopy to ensure the occurrence of fusion.

The Instant Dendritomas were removed from the tissue culture flask by saving the supernatant containing the cells as well by lightly trypsinizing the adherent cells as previously described. The cells were pelleted by centrifugation at 1500 rpm for five minutes. The cell pellet was resuspended in 2 ml of 1× PBS and put into a sterile, polystyrene, round bottom, 12×75 mm Falcon tube. After centrifuging the cells at 1500 rpm for five minutes, they were resuspended in 1 ml of 1× PBS. The Instant Dendritomas were sorted out based on dual green and red fluorescence using a FACS Caliber (Becton Dickinson), using standard methods.

The sorted cells were pelleted by centrifugation at 2000 rpm for 30 minutes. After removing the supernatant, the cells were resuspended at a concentration of 50,000 cells/0.5 ml 1× PBS. A drop of the cells was placed on a slide and evaluated by fluorescent microscopy to ensure the general purity of the sort.

Three days prior to the fusion process, female C57BL/6J. mice were challenged with $0.75 \times 10^6$ B16F0 melanoma cells in 0.4 ml 1× PBS by intravenous injection. Once the Instant Dendritomas were pelleted and resuspended, each mouse was injected intravenously with 50,000 cells. This was followed by IL-2 treatment, which was administered intraperitoneally at 10,000 IU/day/mouse. The mice were monitored up to four weeks for pulmonary metastasis.

At the end of four week, the mice were sacrificed and the metastases were counted. Each of the four control animals, which were not treated with the Instant Dendritomas, had greater that 50 tumors. On the other hand, only one of the treated animals had measurable metastases. These data indicate that the present hybrid cells are effective in treating cancer in proven animal model system. The data are compiled in the following table.

| GROUP | Number of Metastases (including tumors at non-lung sites) |
|---|---|
| Control | |
| A | >50 |
| B | >50 |
| C | >50 |
| D | >50 |
| Experimental | |
| A | 0 |
| B | 3 |
| C | 0 |
| D | 0 |

Example 2

Human Studies

This example demonstrates that the inventive dendritoma hybrid cells induce a cancer cell-specific cytotoxic T cell response. This offers proof of principle that these hybrid cells can induce a therapeutically meaningful immune response against a tumor.

In order to enhance the number of dendritic cells, which were isolated from peripheral blood, a panning technique using anti-CD14 coated plates was utilized. Five hundred micrograms of anti-CD14 antibody was resuspended in 5 ml of 1× PBS with BSA (700 μg of BSA per 100 μl of antibody). A 100 mm tissue culture plate was coated with 5 mls of the antibody. The plate was swirled and incubated for one hour at room temperature or overnight at 4° C. The antibody solution was removed, and the plate was washed five times with 5 mls of 1× PBS.

Peripheral blood mononuclear cells (PBMC's) were isolated from whole blood by obtaining 50 ml of peripheral blood from the patient in preservative-free or sodium heparin tubes. The blood was diluted 1:1 with 1× PBS. Eight ml of the diluted blood was layered over 4 ml of room temperature Ficoll-Paque Plus in 15 ml conical centrifuge tubes. The Ficoll gradients were centrifuged at 400 g at room temperature for 40 minutes. Using a Pasteur pipet, the PBMC layers were carefully removed from the Ficoll gradient and put into a clean 15 ml centrifuge tube. Four volumes of 1× PBS were added to the tube and inverted several times to mix thoroughly. The PBMC's were centrifuged at 100 g at room temperature for 10 minutes. After removal of the supernatant, 10 ml of 1× PBS was added to the cell pellet and inverted to mix. The PBMC's were pelleted by centrifugation at 100 g at room temperature for 10 minutes. The supernatant was removed, and the PBMC's were resuspended in 5 ml complete DC medium (RPMI 1640, 10% Human Serum, 800 U/ml GMCSF, 1000 U/ml IL-4, 100 μg/ml gentamicin).

The resuspended PBMC's (up to $2 \times 10^8$) were pipetted onto the anti-CD14 coated plate and swirled to cover the entire plate. The plate was incubated at room temperature for 30 minutes. After gently swirling the plate again, the supernatant containing the non-adherent cells was removed. The adherent cells were washed by adding 10 ml of 1× PBS and swirling. This wash was repeated for a total of four times, pipetting at the same place each time. Immediately after the washes, 10 mls of complete DC media was added to the plate. The culture was incubated at 37° C., 5% $CO_2$ for 5 to 10 days to generate dendritic cells.

A section of tumor that had been resected from a patient was received immediately after the surgery. The section of tumor was cut into several pieces and placed in a 50 ml conical centrifuge tube containing 1× PBS. The tumor pieces were further cut into smaller pieces using sterile dissection scissors and placed into a T75 tissue culture flask. Ten ml of 0.25% Trypsin/EDTA was added to the flask, which was incubated at 37° C. with rocking for one hour. Following incubation, 15 ml of complete tumor cell media (DMEM, 10% Human Serum, 200 μg/ml gentamicin) was added to the flask. The tumor pieces were removed and placed into a clean T75 flask, which was incubated overnight at 37° C., 5% $CO_2$.

The medium/trypsin mixture from the original flask contained some single tumor cells. These cells were filtered through a 40 μm cell strainer and pelleted by centrifugation at 1500 rpm for five minutes. The cells were resuspended in 10 ml of complete tumor cell media and put into a T75 tissue culture flask and incubated at 37° C., 5% $CO_2$. To the flask containing the tumor pieces, 20 ml of complete tumor cell media was added after the overnight incubation. Both flasks were carefully monitored for attaching cells. After several days, the tumor pieces were removed from the flask. The attached tumor cells were fed every three days and maintained for experimental use. They were subcultured using standard tissue culture techniques for adherent cells.

Cell membrane labeling of human dendritic cells and tumor cells were prepared as described in Example 1, above.

CD8+, cytotoxic T cells (CTLs) were prepared by the following method. Peripheral blood mononuclear cells (PBMC's) were isolated from whole blood by obtaining 40 ml of peripheral blood from the patient in preservative-free or sodium heparin tubes and 10 ml in ACD tubes. The blood was diluted 1:1 with 1× PBS. Eight ml of the diluted blood was layered over 4 ml of room temperature Ficoll-Paque Plus in 15 ml conical centrifuge tubes. The Ficoll gradients were centrifuged at 400 g at room temperature for 40 minutes. Using a Pasteur pipet, the PBMC layers were carefully removed from the Ficoll gradients and put into a clean 15 ml centrifuge tube. Four volumes of 1× PBS were added to the tube and inverted several times to mix thoroughly. The PBMC's were centrifuged at 100 g at room temperature for 10 minutes. After removal of the supernatant, 10 ml of 1× PBS was added to the cells and inverted to mix. The PBMC's were pelleted by centrifugation at 100 g at room temperature for 10 minutes and resuspended in complete lymphocyte media (RPMI 1640, 10% FBS, 100 μg/ml gentamicin).

PBMC's were isolated from patients in preservative-free or sodium heparinized blood. They were subjected to the same panning technique as previously described except that anti-CD4 antibody was used to coat the plate. Prior to panning the PBMC's were enriched for T lymphocytes by passing them through a nylon wool column. This was done by packing 0.5 g of teased nylon wool into a 10 ml syringe which has a stopcock attached to the tip. The column was washed twice at 37° C. with RPMI 1640 with 10% FBS. The stopcock was closed and incubated at 37° C. for one hour. After draining the media from the column to the top of the wool, the PBMC's were added to the column (up to $2 \times 10^8$ in 2 ml of media). The stopcock was opened the media was drained until the cell volume had entered the packed wool. After closing the stopcock additional media was added to cover the top of the wool. The column was incubated for one hour at 37° C. The nonadherent T cells were collected by two media washes. After this T cell enrichment, the T lymphocytes were panned using the anti-CD4 coated plate. T cells that were not bound by the CD4 antibody were recovered and assumed to be CD8+ cells (cytotoxic T lymphocytes). This was confirmed by FACS analysis.

In order to have constant re-stimulators for tumor cell specific CTL's, the PBMC's isolated from the ACD blood were immortalized by Epstein-Barr virus (EBV) transformation. This was accomplished by resuspending the PBMC's at a concentration of $1 \times 10^6$ cells/ml complete lymphocyte media. To this, 1 ml of EBV supernatant and 0.2 ml of phytohemagglutinin were added. The cell mixture was cultured in a T25 tissue culture flask at 37° C., 5% $CO_2$.

The Instant Dendritomas obtained from the FACS sort were mixed with the enriched, panned CD8+ T lymphocytes in a 1:10 ratio. The CD8+ cells to be used were pelleted by centrifugation at 1500 rpm for five minutes and resuspended in 1 ml of medium containing RPMI 1640, 10% FBS, 1000 U/ml IL-6, 5 ng/ml IL-12, and 10 U/ml IL-2. This was added to the Instant Dendritomas plated after the sort. This culture was incubated at 37° C., 5% $CO_2$ for one week. During that week the cells were refed with the same media.

After one week, the primed CD8+ T cells (CTL's) were restimulated with irradiated EBV-transformed lymphocytes that were pulsed with tumor lysate. Tumor cells, which had been previously cultured, were subjected to four freeze thaw cycles to lyse the cells. To obtain the lysate containing tumor antigens, the lysed cells were centrifuged at 600 g for ten minutes. The supernatant was collected and centrifuged at 13,000 g for one hour. The supernatant contain the lysate of tumor antigens was collected. To restimulate the CTL's a viable cell count was taken using trypan blue exclusion. Once the viable cell number was determined the same number of EBV transformed lymphocytes were pulsed with the tumor lysate by incubating the lysate with the lymphocytes at 37° C., 5% $CO_2$ for one hour. The pulsed lymphocytes were irradiated with 5,000 rads and then mixed with the CTL's in media containing RPMI 1640, 10% FBS, 10 U/ml IL-1α, 5 U/ml IL-2, 50 U/ml IL-4, 125 U/ml IL-6, and 30 U/ml IL-7. The culture was incubated at 37° C., 5% $CO_2$ and refed every two days. This re-stimulation was performed at 7 and 14 days after initial priming.

Each day the CTL's were refed, the supernatant that was removed was stored at −20° C. When feasible, an Interferon-gamma (IFN-γ) assay was performed using an OptEIA Human IFN-γ Kit (PharMingen). The protocol was performed exactly according to the manufacturer's directions. The assay was read using a Benchmark Microplate Reader (BioRad).

To determine if the Instant Dendritomas stimulated a tumor cell specific CTL response, a CTL assay was performed using the cultured tumor cells as target cells. Fifty thousand tumor cells were harvested and pelleted in a 15 ml conical centrifuge tube by centrifugation at 200 g for five minutes. The supernatant was discarded leaving 0.1 ml of medium on the pellet. The cells were gently resuspended in the remaining medium. The tumor cells were then labeled with $^{51}Cr$ by adding 0.1 ml of 1 mCi/ml $^{51}Cr$ solution and 10 μl FBS and mixing gently. This mixture was incubated by loosening the cap of the tube and placing at 37° C., 5% $CO_2$ for one hour. After the incubation, the labeled tumor cells were washed twice with 14 ml of RPMI 1640 and resuspended at a concentration of $5\times10^4$ cells/ml in complete lymphocyte media.

The CTL effector cells were plated in 4 wells of a round bottom 96 well tissue culture plate at concentrations that equaled 100:1, 30:1, 10:1, and 3:1 effector to target cell ratios. Five thousand labeled target cells were added to the wells containing the effector cells as well as two additional wells for natural and maximum release controls. The cells were mixed and centrifuged at 200 g for 30 seconds. The plate was then incubated at 37° C., 5% $CO_2$ for four hours. Thirty minutes prior to the end of the incubation, 0.1 ml of Triton X-100 was added to the maximum release control well. At the end of the incubation, the cells were centrifuged in the plate at 200 g for five minutes. 0.1 ml of each supernatant was added to liquid scintillation counter vials containing 5 ml of scintillation cocktail. The amount of $^{51}Cr$ release was measured using a LS6500 Multi-purpose Scintillation Counter (Beckman).

Figure 1:
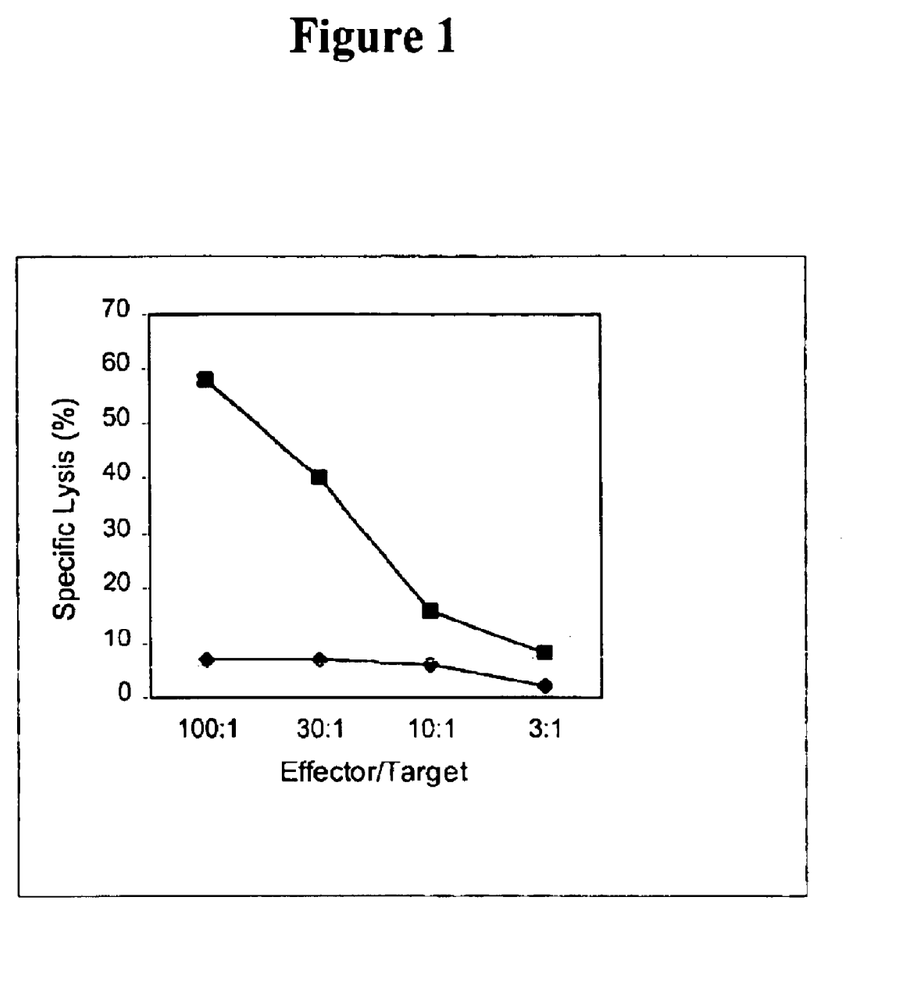
FIG. 1 shows that hybrid cells according to the invention, between dendritic cells and cancer cells are capable of generating a tumor-specific cytotoxic T cell response, which is relevant to in vivo immunotherapy.

The CTL assay results showed that as the ratio of hybrid cell-primed CTLs to tumor cells increased, the release of the isotope increased, indicating a positive correlation between the number of CTLs and tumor killing. Greater than 50% killing was observed at a 100:1 effector:target ratio. On the other hand, there was no such correlation with control T cells that were not primed with the inventive hybrid cells. Even at a ratio of 100:1, the control T cells did not lyse more tumor cells than at lower ratios. These results demonstrate that the CTLs generated using our hybrid antigen presenting cells are fully functional and tumor cell specific. The results are depicted in FIG. 1.

In fact, these data provide proof of the principal that the present hybrid cells can be used in immunotherapy in vivo. CTLs are known to play a vital role in the cell mediated immune response, i.e., they are primarily responsible for killing the cells bearing "foreign" antigens. A principle behind using immunotherapy to treating cancer, for example, is based on stimulating tumor cell-specific CTLs, which results in tumor cells killing. The fact that the inventive hybrid cells are able to stimulate a tumor-specific T cell response provides compelling evidence that they will be useful in in vivo immunotherapy, via the same mechanism.

Example 3

Dendritoma Characterization

This example provides further characterization of the reactant cells and the dendritomas described in Examples 1 and 2.

Fluorescent microscopic analysis showed that 100% of the stained cells were successfully labeled. To test whether the dye can interstain between the two different type of cells, green DCs and red tumor cells were mixed together and incubated overnight. Fluorescent microscopic examination showed there was no interstaining. Immediate examination of the fusion product demonstrated that the green DCs and the red tumor cells were fused together and after an overnight recovery, the fused cells showed both colors. The double colored cells (approximately 10% of the total cells), instant dendritomas, were then purified by FACS sorting. More than 95% of the sorted cells were double colored fused cells.

Figure 2A:
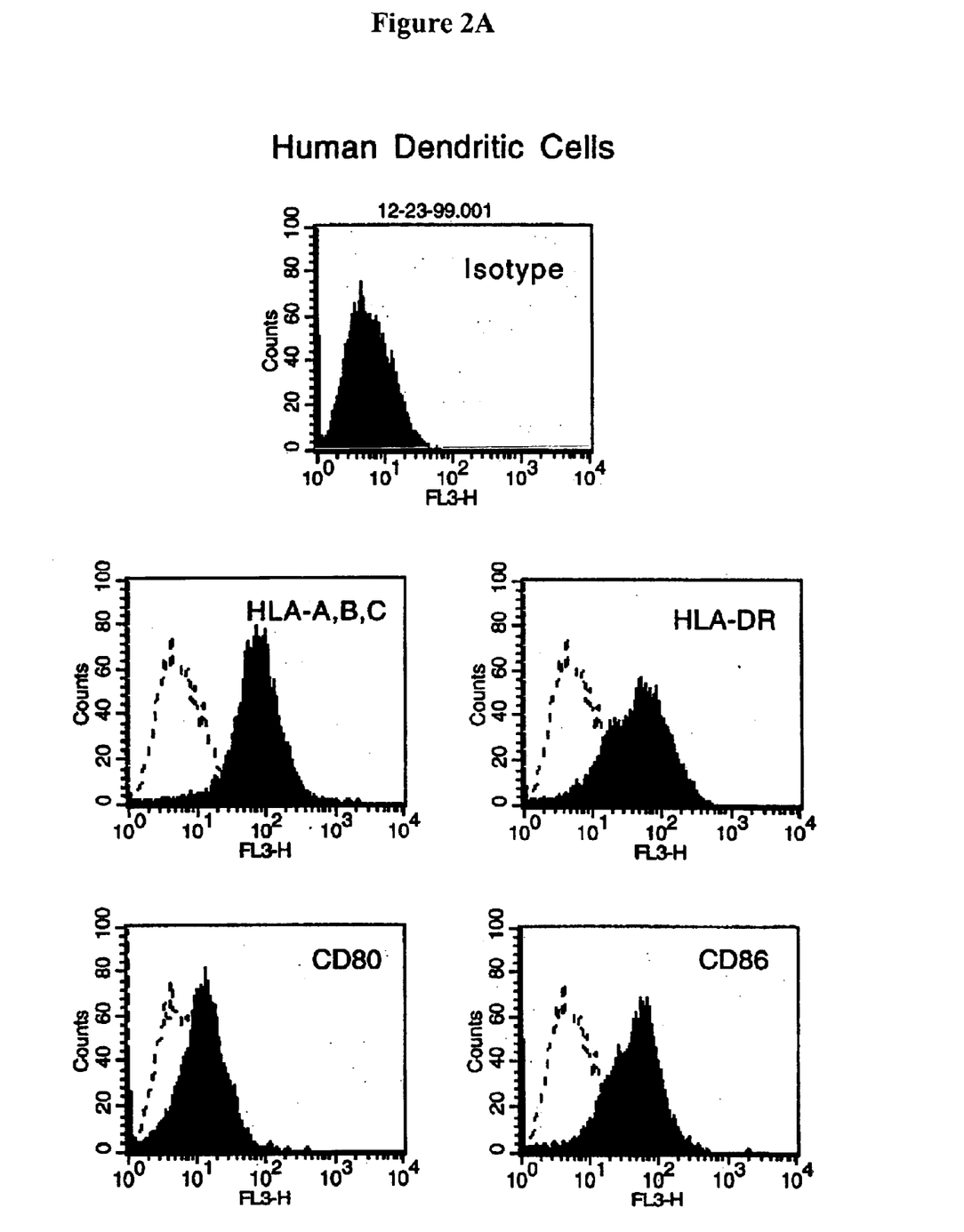
FIG. 2A shows FACS-detection of antigen-presentation markers on control dendritic cells. A normal distribution is shown.
Figure 2B:
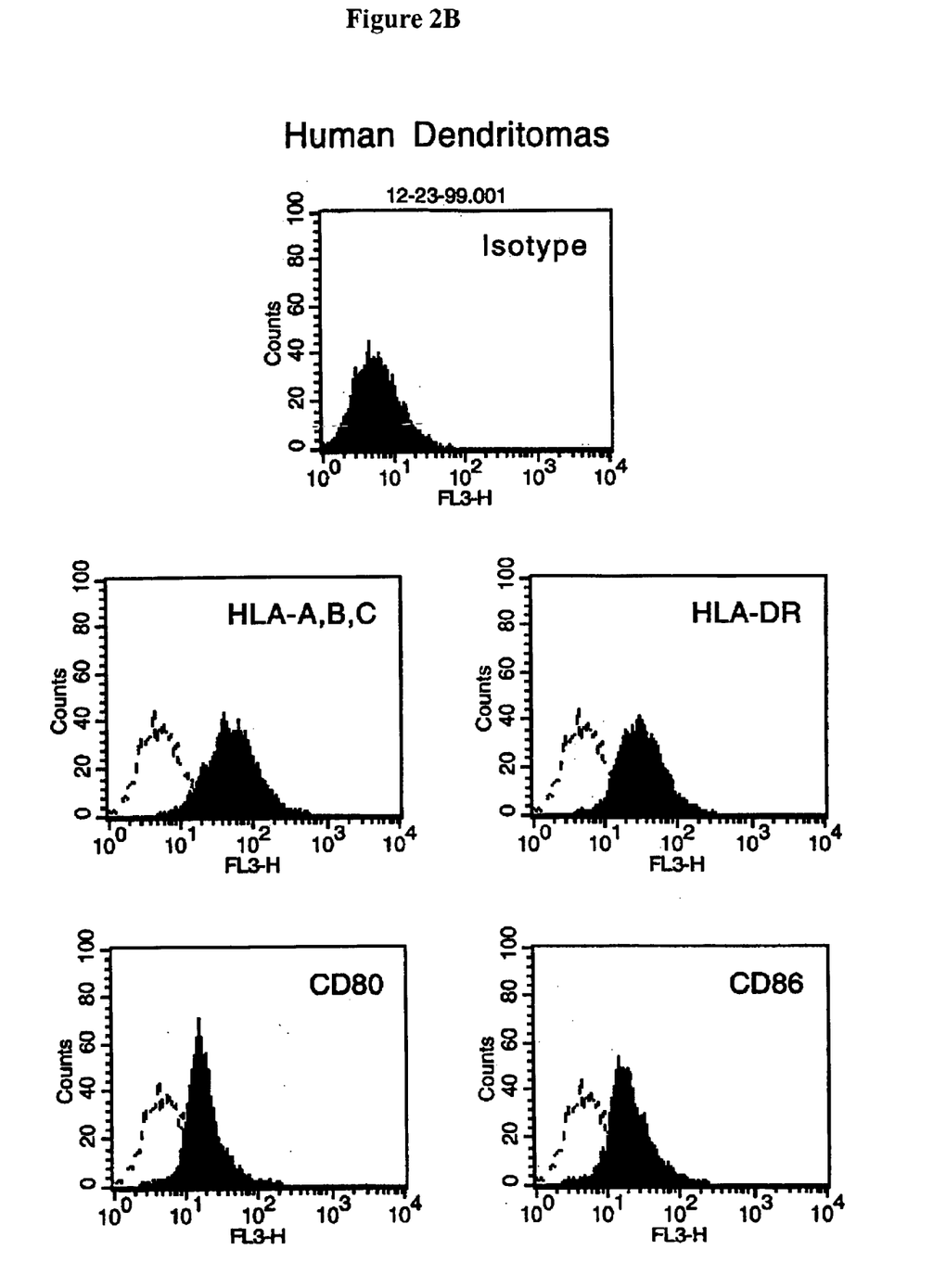
FIG. 2B shows FACS-detection of antigen-presentation markers on dendritic/tumor cell hybrids. A normal distribution is shown, as compared to the control dendritic cells, meaning that the hybrid cells retain all of the markers necessary for antigen presentation.

Instant dendritomas express all the molecules necessary for antigen presentation. FACS analysis showed that instant dendritomas express the molecules required for antigen presentation, such as MHC class I and II and co-stimulating molecules CD80 (B7.1) and CD86 (B7.2). The data are depicted in FIG. 2. "Isotype" is the negative control; HLA-A,B,C is MHC class I and HLA-DR is MHC class II. Under microscope, moreover, instant dendritomas also have those dark granules that melanoma tumor cells have.

For FIG. 2, human DCs from peripheral blood were stained with the green dye and tumor cells were stained with the red dye, respectively, and fused, using the above protocol. After overnight incubation, the cells were equally divided into 4 groups. They were then stained with Cy-Chrome conjugated antibodies by incubating the cells with the antibodies (1 million cells/microgram antibody, Becton/Dickinson) on ice for 30 min. The different groups were as follows: anti-human HLA-A,B,C [group I]; anti-human HLA-DR [group II]; anti-human CD80 [group III]; and anti-human CD86 [group IV]. The un-bound antibodies were removed by two washes and the cell pellet was re-suspended in 0.5 ml of staining buffer (PBS containing 0.1% BSA and 0.1% sodium azide). Three-color analysis was performed by FACS, using CellQuest software. Control human DCs were also stained with the same antibodies in the same way.

Example 4

Clinical Protocol

This example provides an exemplary clinical protocol for treating human cancer patients with the inventive hybrid cell preparations. This regimen is useful, for example, to treat melanoma patients with a dendritoma, prepared according to the inventive methodologies.

Mature dentritic cells are generated from the patient's peripheral blood monocytes. 50 mls of peripheral blood are obtained from the patient in preservative free or sodium heparin tubes. Briefly, the blood are diluted 1:1 with 1× PBS. Then, 8 mls of the diluted blood are layered over 4 mls of room temperature Ficoll-Paque Plus in a 15 ml centrifuge tube, and centrifuged at 40 g for 40 minutes. The PBMC layer is removed from the Ficoll gradient, and placed into a clean 15 ml centrifuge tube. 4 volumes of 1× PBS are added and the tube is inverted to mix. The PBMC's are then centrifuged at 100 g at room temperature for 10 minutes. 10 mls of 1× PBS are added, and the cells are mixed by inverting the tube. The PBMC's are again centrifuged at 100 g at room temperature for 10 minutes. The PBMC's are resuspended in 5 mls complete DC medium (RPMI 1640+ 10% human serum +800 U/ml GMCSF+1000 U/ml IL-4). Then the dendritic cells/precursors are panned using anti-CD14 coated plates. $2\times10^8$ PBMC's are placed onto the anti-CD14 coated plate and swirled. They are left to incubate at room temperature for 30 minutes. The non-adherent cells are then removed. 10 mls of 1× PBS are added, the plate is swirled, and the PBS is removed. This PBS washing is repeated for a total of four times, pipetting at the same place each time. Afterwards, 10 mls of complete DC media is added to the plate. They are then incubated at 37° C., 5% $CO_2$ for 5–10 days to generate dendritic cells.

A tumor section obtained at the time of biopsy or excisional resection. The tumor cells are cultured using the following technique. After separating fat and necrotic tissue away from the tumor tissue (1–5 grams), the tumor are cut into small chunks and put into a T 75 flask. 10 mls of 0.25%

Trypsin-EDTA are added. This solution will rock for 1 hour at 37° C., and then 15 mls of complete media (DMEM+10% human serum+gentamicin) are added. The chunks are then removed and put into a clean T75 flask. This flask is left at 370 C in 5% CO2 overnight. Then the cell suspension/ typsin/complete media is centrifuged at 1000 g for 5 minutes. These cells are resuspended in 15 mls of complete media and cultured in a T75 flask at 37° C. in 5% CO2 for 24 hours. After overnight incubation in the absence of media, 20 mls of complete media are added to the flask with chunks, and this solution is left for two days at 37° C. in 5% CO2. The chunks are removed, and the adherent cells are cultured. The tumor cells used for dentritic fusion result from both cultures.

The next step involves the fusion of tumor cells and dendritic cells received from the patient. Hybrid formation by cell fusion became routine after the introduction of the use of polyethylene glycol as a fusing agent. The procedure outlined below is a variation of the one reported by Prado et al., 1989 FEBS Lett., 259: 149–52., for the PEG-mediated fusion of somatic cells in monolayers.

First, the tumor cells are exposed to a single dose of 5000 rads, sufficient to kill all of the cells. Then, the dendritic cells are stained green using the PKH2-GL fluorescent dye (Sigma), and the tumor cells are stained red using the PKH26 fluorescent dye (Sigma). The staining procedure is performed at 25° C., using a slight modification of the Sigma procedure. The cells to be stained are washed with serum-free media. The cell suspension is centrifuged at 400 g for five minutes to obtain a loose pellet, and the supernatant fraction is removed. The pellet is resuspended by tapping the centrifuge tube, and 1 ml of Diluent (20% DMSO in serum-free RPMI) is added to resuspend the cells. Immediately prior to staining, $4 \times 10^{-6}$ molar dyes (2x) were prepared with Diluent in polypropylene tubes. The cells in the diluent are rapidly added into 1 ml of 2x dye, and the mixture is immediately mixed by gentle pipetting. The mixture is then incubated at 25° C. for five minutes. The staining process is stopped by adding an equal volume of 10% human serum, which may be the patient's own serum, and incubating for one minute. The stained cells are diluted with equal volume of complete culture medium. Stained cells are removed from the staining solution by centrifuging at 400 g for 10 minutes.

The green dendritic cells are mixed with the red tumor cells at a 1:1 ratio in a 50-ml conical centrifuge tube. The tube is filled with complete serum-free DMEM. The cell mixture is centrifuged for 5 minutes at 500 g. While the cells are being centrifuged, three 37° C. double-beaker water baths are prepared in the laminar flow hood by placing a 400-ml beaker containing 100 ml of 37° C. water into a 600-ml beaker containing 75 to 100 ml of 37° C. water. Tubes of prewarmed 50% PEG solution and complete serum-free DMEM are placed into two of the 37° C. water baths in the hood. Then, the supernatant from the cell mixture is aspirated and discarded. The cell fusion is performed at 37° C. by placing the tube containing the mixed-cell pellet in on of the double-beaker water baths in the laminar flow hood. Then, 1 ml of prewarmed 50% PEG is added to the mixed-cell pellet drop-by-drop over one minute, stirring the cells with the pipette tip after each drop. The mixture is then stirred for an additional minute.

Using a clean pipette, 1 ml of pre-warmed RPMI+HEPES is added to the cell mixture drop-by-drop over one minute, stirring after each drop. This step is repeated once with an additional 1 ml of prewarmed RPMI+HEPES solution. With a 10-ml pipette, 7 ml of prewarmed RPMI +HEPES is added drop-by-drop over 2 to 3 minutes. This mixture is then centrifuged for five minutes at 500 g. While the cells are in the centrifuge, the water baths are rewarmed to 37° C. and placed in the hood. Prewarmed complete DC media is placed in the beaker water bath. Then the supernatant from the mixture is discarded; the tube is placed in the beaker water bath. With a pipette, 10 ml of prewarmed complete DC media are forcefully discharged onto the cell pellet and placed in a T75 flask. This is incubated overnight in a humidified 37° C., 5% $CO_2$ incubator.

The next day, the cells are analyzed on a FACS Caliber fluorescence activated cell sorter using the CELLQuest software (Becton/Dickenson), which will sort the fusion cells with both the green and red dye. These fusion cells, dendritomas, are then resuspended in 1 ml of NS (Normal Saline) and injected into the patient.

The vaccine will consist of 100,000 (or more) irradiated tumor cells fused to dentritic cells i.e. dendritomas. These dendritomas are resuspended in 1 ml of NS and injected IV into the patient Interleukin 2 (e.g.,, Aldesleukin) also may be given in a low-dose regimen. When used, IL-2 is administered by subcutaneous injection in a dosage of 18 million units daily for 5 days beginning on the day of vaccination.

We claim:

1. A method of preparing a composition for cancer immunotherapy, comprising:
    (a) staining a neoplastic cell population freshly isolated from a patient with a first fluorescent dye,
    (b) staining a dendritic cell population with a second fluorescent dye, wherein said first dye is different from said second dye,
    (c) contacting said neoplastic cell population and said dendritic cell population with one another under conditions that promote cell fusion, and obtaining a resultant hybrid cell population stained with both the first and second dyes,
    (d) purifying the resultant hybrid cell population by fluorescence activated cell sorting, and
    (e) resuspending the resultant hybrid cell population in a pharmaceutically acceptable vehicle;
    wherein said method does not involve antibiotic or metabolic selection, said purifying is accomplished in less than about 24 to 48 hours after said contacting, and the antigenic diversity of the starting neoplastic cell population is preserved in the resultant hybrid cell population.

2. The method of claim 1 wherein the resultant hybrid cell population contains less than 10% of its total population as reactant cells.

3. The method of claim 1, wherein the resultant hybrid cell population contains less than 5% of its total population as reactant cells.

4. The method of claim 1, wherein said pharmaceutically acceptable vehicle is normal saline.

5. A method of preparing a hybrid cell preparation, comprising:
    (a) staining a tumor cell population freshly isolated from a patient with a first fluorescent dye,
    (b) staining a dendritic cell population with a second fluorescent dye, wherein said first dye is different from said second dye,
    (c) contacting said tumor cell population and said dendritic cell population with one another under conditions that promote cell fusion, and obtaining a resultant hybrid cell population stained with both the first and second dyes, and (d) purifying the resultant hybrid cell population by fluorescence activated cell sorting, wherein said method does not involve antibiotic or metabolic selection, said purifying is accomplished in less than about 24 to 48 hours after said contacting, and the antigenic diversity of the starting tumor cell population is preserved in the resultant hybrid cell population.

6. The method of claim 5, further comprising:

(e) resuspending the resultant hybrid cell population in a pharmaceutically acceptable buffer.

7. The method of claim 5 wherein the resultant hybrid cell population contains less than 10% of its total population as reactant cells.

8. The method of claim 5, wherein the resultant hybrid cell population contains less than 5% of its total population as reactant cells.

9. The method of claim 6, wherein said pharmaceutically acceptable buffer is normal saline.

10. The method of claim 5, wherein said first and second fluorescent dyes are endotoxin-free, pyrogen-free or both.

11. The method of claim 5, wherein said tumor cell is a primary tumor cell.

12. The method of claim 1, wherein said first and second fluorescent dyes are endotoxin-free, pyrogen-free or both.

13. The method of claim 1, wherein said neoplastic cell is a tumor cell.

14. The method of claim 13, wherein said tumor cell is a primary tumor cell.

* * * * *